United States Patent [19]

Zuckermann et al.

[11] Patent Number: 5,252,296
[45] Date of Patent: Oct. 12, 1993

[54] METHOD AND APPARATUS FOR BIOPOLYMER SYNTHESIS

[75] Inventors: Ronald N. Zuckermann, Berkeley; Verena D. Heubner, Benicia; Daniel V. Santi, San Francisco; Michael A. Siani, Oakland, all of Calif.

[73] Assignee: Chiron Corporation, Emeryville, Calif.

[21] Appl. No.: 652,194

[22] Filed: Feb. 6, 1991

Related U.S. Application Data

[63] Continuation-in-part of Ser. No. 523,791, May 15, 1990, Pat. No. 5,182,366.

[51] Int. Cl.$^5$ .............................................. G05D 7/00
[52] U.S. Cl. ..................................... 422/116; 422/131; 422/135; 435/289; 935/88
[58] Field of Search ............... 422/116, 131, 135; 435/289; 935/88

[56] References Cited

U.S. PATENT DOCUMENTS

| | | | |
|---|---|---|---|
| 5,053,454 | 10/1991 | Judd | 422/116 |
| 5,080,866 | 1/1992 | Petty et al. | 422/116 |
| 5,104,808 | 4/1992 | Laska et al. | 422/116 |
| 5,112,575 | 5/1992 | Whitehouse et al. | 422/116 |

OTHER PUBLICATIONS

Fodor, S.P.A., et al., Science (15 Feb. 1991) 251:767–773.
Cwirla, S. E., et al., Proc. Natl. Acad. Sci. (U.S.A.), (1990) 87:767–773.
Tjoeng, F. S., et al., Int. J. Pept. Prot. Res., (1990) 35:141.
Geysen, H. M. et al., Proc. Natl. Acad. Sci. (U.S.A.), (1984) 81:3998.
Houghten, R. A., et al., Proc. Natl. Acad. Sci. (U.S.A.), (1985) 82:5131–5135.

Primary Examiner—Timothy M. McMahon
Attorney, Agent, or Firm—Peter J. Dehlinger

[57] ABSTRACT

Method and apparatus for synthesizing biopolymers, such as polypeptides and polynucleotides. The apparatus includes plural reaction vessels in which subunit coupling to biopolymers in a particle suspension is carried out. The vessels are connected to common valving structure for use in mixing the suspension and removing suspension liquid. In one embodiment, a robotic arm in the apparatus is operable to transfer reaction solution to the reaction vessels, and to transfer particle suspensions from the reaction vessels to a mixing vessel and back to the reaction vessels. The method can be used to produce preferably equi-molar amounts of different-sequence biopolymers, such as polypeptides and polynucleotides.

6 Claims, 9 Drawing Sheets

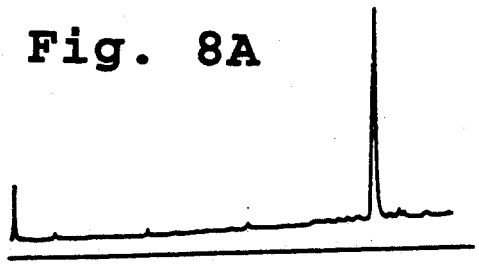
Fig. 8A  R(Mts)-V-P-DF-L-L-V-P-DF-L
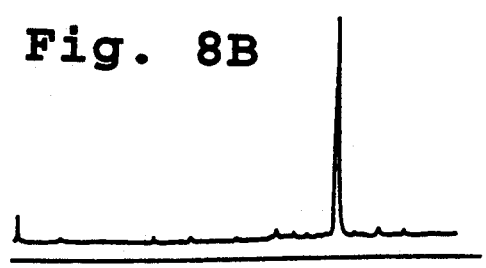
Fig. 8B  R(Mts)-V-P-DA-L-L-V-P-DF-L
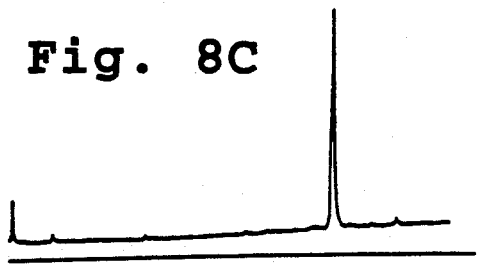
Fig. 8C  R(Mts)-V-P-DF-L-L-V-P-DA-L
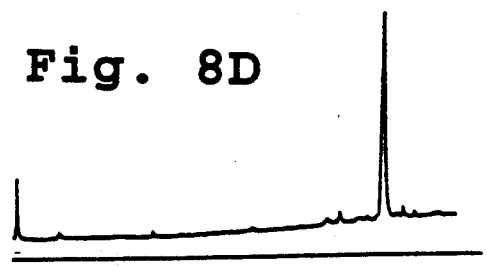
Fig. 8D  R(Mts)-V-P-DA-L-L-V-P-DA-L
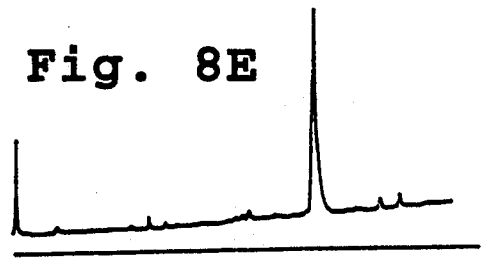
Fig. 8E  R(Mts)-V-P-DF-L-F-V-P-DA-L
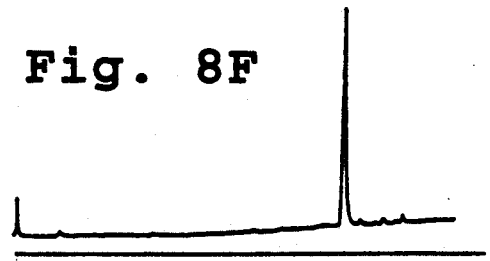
Fig. 8F  R(Mts)-V-P-DF-DA-L-V-P-DF-A
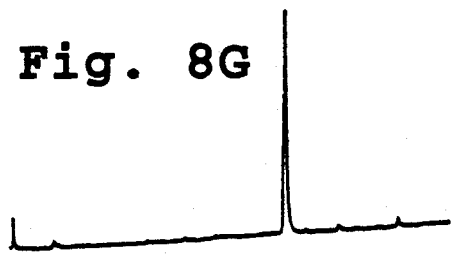
Fig. 8G  R(Mts)-V-P-DF-L-L-V-P-S-L

METHOD AND APPARATUS FOR BIOPOLYMER SYNTHESIS

This application is a continuation-in-part of U.S. patent application for "Controlled Synthesis of Peptide Mixtures Using Mixed Resins," U.S. patent application Ser. No. 523,791, filed May 15, 1990 now U.S. Pat. No. 5,182,366; this application is incorporated herein by reference.

FIELD OF THE INVENTION

The present invention relates to method and apparatus for synthesis of biopolymers, such as polypeptides and polynucleotides.

REFERENCES

Bidlingmeyer, B. A. et al, in Rivier, J. et al (eds.) Peptides: Chemistry, Structure and Biology (proceedings of the 11th American Peptide Symposium), ESCOM, Leiden, 1990, p.1003.
Cwirla, S. E., et al., Proc Nat Acad Sci, USA, 87:6378 (1990).
Geysen, H. M., et al, Proc Nat Acad Sci USA, 81:3998 (1984).
Houghten, R. A., Proc Nat Acad Sci, USA, 82:5135 (1985).
Kaiser, E. et al, Anal Biochem, 34:595 (1970).
Parmley, S. F., et al, Gene, 73:305 (1988).
Schnorrenberg, G., et al, Tetrahedron, 45:7759 (1989).
Scott, J. K., et al., Science, 249:386 (1990).
Tjoeng, F. S., et al., Int J Pept Prot Res, 35:141 (1990).
Tjoeng, F. S., eds.

BACKGROUND OF THE INVENTION

Defined-sequence biopolymers, such as polypeptides and polynucleotides, are routinely synthesized by solid-phase methods in which polymer subunits are added stepwise to a growing polymer chain immobilized on a solid support. The general synthetic procedure can be carried out with commercially available synthesizers which can construct defined sequence biopolymers in an automated or semi-automated fashion. Heretofore, however, commercially available synthesizers have been limited by the total quantity of polymer which can be synthesized in a single operation.

Increasingly, there is an interest in synthesizing biopolymer mixtures containing different-sequence biopolymers. For example, it is often of interest, in examining structure-function relationships in peptides, to generate a mixture of peptides having different amino acid substitutions at one or more defined polypeptide residue positions. As another example, polypeptides having a desired activity, such as a high binding affinity to a given receptor or antibody, may be identified by (a) generating a large number of random-sequence peptides, and (b) screening these peptides to identify one or more peptides having the desired binding affinity. Preferably, the polypeptides in the mixture are present in substantially equimolar amounts, to maximize the possibility of detecting any one sequence out of large number of sequences, and in molar amounts which allow detection of a single sequence.

Although methods have been proposed for synthesizing mixtures of different-sequence peptides (e.g., Houghton, Geysen), such methods are limited in both the number and quantity of different sequence polypeptides which can be synthesized in a single operation, and also are relatively expensive to carry out. These limitations have restricted the availability of different-sequence peptides, both for structure-function studies, or for polypeptide selection methods.

SUMMARY OF THE INVENTION

It is one general object of the invention to provide a method and apparatus for efficient synthesis of biopolymers, such as polypeptides and polynucleotides, formed by subunit addition to terminal subunits immobilized on solid-phase particles.

Another object of the invention is to provide such method and apparatus for use in synthesizing mixtures of different-sequence biopolymers.

In one aspect, the apparatus of the invention includes a plurality of reaction vessels in which subunit addition reactions to polymer subunits immobilized on solid-phase particles are carried out. The vessels have bottom-portion particle filters which are connected to vacuum and compressed gas sources by valve structure operable, in a closed condition, to isolate the vessels from the sources, and, in an open condition, to communicate the vessels with the gas source, for bubbling gas into the vessels for particle-suspension mixing, or with the vacuum source, for removing suspension liquid from the vessels. A control unit in the apparatus operates to place the valve structure in selected conditions for mixing and removing a series of subunit-addition solutions added sequentially to the vessels.

The reaction vessels are preferably configured in multiple sets of vessels, and these sets are valved in a configuration which allows valve control over any selected number of reaction vessels.

The apparatus may further include reagent vessels for holding the solution reagents used in subunit addition, and a transfer device operable to transfer solutions from the reagent vessels to each of the transfer vessels. The control unit in this apparatus is operable, with a suspension of solid-phase particles in the reaction vessels, to:

(i) activate the valve structure to communicate the vacuum source with the reaction vessels, to remove liquid in which the solid-phase particles are suspended, (ii) activate the transfer device to transfer solution reagent from a selected reagent vessel to each of the reaction vessels, (iii) activate the valve structure to communicate the compressed gas source with each reaction vessel, to produce bubbling in each vessel for mixing the solid-phase particles with the added reaction solution in each vessel, and (iv) repeat steps (i)–(iii) until each reagent solution required for subunit addition to the subunits immobilized on the particles has been added to the vessels.

The apparatus may further include one or more mixing vessels to which particle suspensions from the reaction vessels can be transferred, by the transfer device, for forming a mixed-particle suspension. After mixing, the suspension can be distributed, by the transfer device, to selected reaction vessels.

In another aspect, the invention includes an apparatus for use in an automated mixed-particle method for biopolymer synthesis. The apparatus includes multiple reaction vessels, preferably constructed as above, reagent vessels, a mixing vessel, and a transfer device for distributing a selected volume of particle suspension in the mixing vessel to each of the reaction vessels, for transferring a particle suspension from each reaction vessel to the mixing vessel, and for transferring selected reagent solutions from the reagent vessels to the reaction vessels. Operation of the transfer device, for carrying out successive mixed-particle subunit coupling reactions, and for mixing and redistributing particle suspensions, is by a control unit.

The apparatus is designed for an automated method of synthesis of a mixture of different-sequence biopolymers. In carrying out the method, the apparatus operates to distribute to each of a plurality of reaction vessels, a particle suspension composed of a suspension of solid-phase particles derivatized with particle-bound biopolymer terminal subunits. A selected subunit is then coupled to the particle-bound terminal subunits in each reaction vessel by successive addition to, reaction with, and removal of coupling reagent solutions, as above. A suspension of particles in each reaction vessel is now withdrawn from the reaction vessels, transferred to a mixing vessel, mixed to form a mixed-particle suspension, and redistributed to separate reaction vessels. The cycle is repeated until different-sequence biopolymers of a desired length are synthesized.

In one preferred embodiment, the particles are polystyrene particles, and the suspension solution includes DMF/methylene chloride in substantially equal volume amounts.

More generally, the invention provides a method of synthesizing a mixture of biopolymers having different selected subunits at selected subunit positions. In practicing the method, there is formed a particle suspension composed of a mixture of solid-phase particles derivatized with different terminal particle-bound biopolymer subunits. This suspension is distributed into a plurality of separate reaction vessels, where a different selected subunit is coupled to the particle-bound terminal subunits in each vessel. After subunit addition, a suspension of particles from each vessel is mixed and redistributed to separate reaction vessels. The cycle is repeated until the desired length, different-sequence biopolymers are formed.

The method is useful, when applied to polypeptide synthesis, for determining the effect of amino acid substitutions at selected residue positions on a given activity of a known-sequence polypeptide, and for producing a polypeptide having a selected binding activity to a receptor.

The method is useful, when applied to polynucleotide synthesis, for synthesizing polynucleotides with random coding sequences. The random sequences may be selected for expression of a polypeptide having a selected binding activity to a receptor or the like, or for production of novel peptide therapeutic and diagnostic agents.

These and other objects and features of the invention will become more fully apparent when the following detailed description of the invention is read in conjunction with the accompanying drawings.

BRIEF DESCRIPTION OF THE DRAWINGS

FIGS. 8A–8G are HPLC chromatographs of single-sequence polypeptides formed in accordance with one aspect of the invention;

DETAILED DESCRIPTION OF THE INVENTION

I. Automated Biopolymer Synthesis Apparatus

Figure 1:
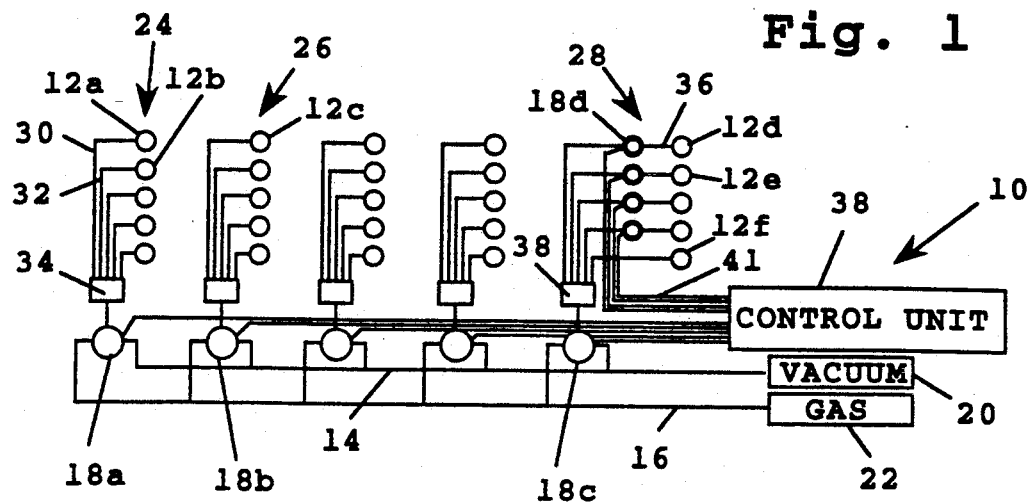
FIG. 1 is a diagrammatic view of a multi-vessel biopolymer synthesis apparatus constructed according to one embodiment of the invention.

FIG. 1 is a schematic view of a biopolymer synthesis apparatus 10 constructed according to one embodiment of the invention. The apparatus includes a plurality of reaction vessels, such as vessels 12a–12f, which are each connected to a vacuum manifold 14 and to a compressed gas manifold 16 through valves, such as valves 18a–18d. The apparatus is designed for use with a vacuum source 20 and a source 22 of compressed gas, preferably an inert gas such as argon, by connection of the vacuum and gas manifolds with the vacuum and gas sources, respectively, as shown. Each valve is operable between a closed position, in which the vessels connected to the valve are isolated from the vacuum and gas sources, and open positions, in which the vessels are in communication with the vacuum manifold, in one open position, and with the gas manifold, in another open position.

In the configuration shown, the vessels are divided into five sets of vessels, such as sets 24, 26, 28. In four of these sets, each of five vessels is connected by tubes, such as tubes 30, 32, to a valve manifold, such as manifold 34, which in turn is connected to a valve, such as valve 18a. Thus, each vessel in the set is coordinately communicated with the vacuum and gas manifold by a single valve. In the fifth set, four of the vessels are connected to individual valves, such as valve 18d connected to vessels 12d, by a tube, such as tube 36. These individual valves, and the fifth vessel in this set, are connected to a valve manifold 38 connected to valve 18c, which thus functions as a master valve for the vessels in this set.

It will be appreciated that the valve configuration just described allows active valve control, by a relatively small number of valves, over any selected number of vessels in the apparatus. Thus, for example, a single vessel 12f can be placed under individual control of valve 18c, with all of the other valves placed in a closed position. Similarly any number of vessels up to five can be placed under control of valve 18c, and one of the individual-control valves, such as valve 12e. (Only four such individually controlled vessels are needed, since five vessels can be controlled by a single valve in one of the other vessel sets. Further, two of these four could be placed under control of a single valve, and still allow control of 1–4 vessels). For five or more vessels, one or more of the five-vessel sets are employed and any individual vessels in the fifth set.

Figure 2:
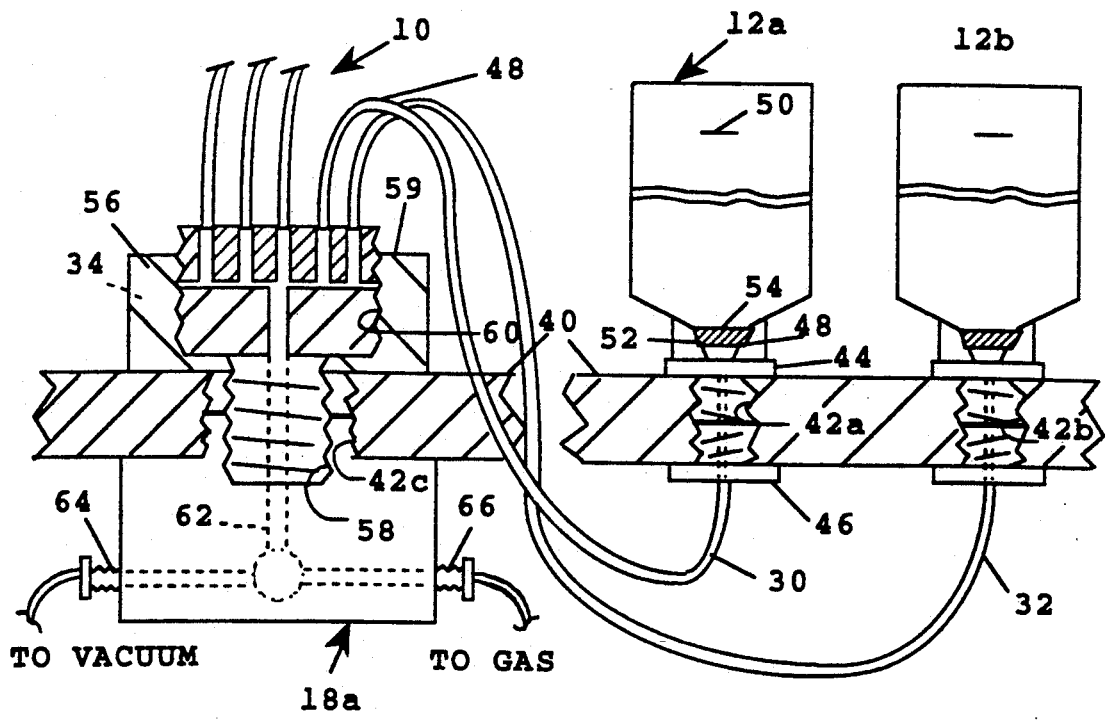
FIG. 2 is a cross-sectional view of fragmentary portions of the FIG. 1 apparatus, showing the valve and tubing connections between a solenoid valve and two reaction vessels.

FIG. 2 is a cross-sectional view of the apparatus, showing reaction vessels 12a and 12b, and their connection to valve 18a. The valves and vessels in the apparatus are carried on a platform 40 which has an array of threaded openings, such as opening 42a, 42b, 42c, for valve and vessel mounting. Vessel 12a, which is representative, is removably mounted on a Luer-Lok TM-type bulk-head fitting 44 which itself is threadedly received in the upper side of opening 42a. A tube fitting 46 is received in the lower side of the opening, as shown. Tube 30, which connects vessel 12a to valve 18a, is received through the two fittings and held tightly therein. An exemplary Teflon Luer-Lok TM fitting, and an exemplary Teflon tube fitting for use with a 1/16" Teflon TM connecting tube are available from Cole-Parmer (Chicago, Ill.).

Connecting tube 30, which is representative, has an upper looped portion 48 which extends above the height of liquid added to vessel 12a during apparatus operation. This height is indicated by the mark 50 on vessel 12a. The tube upper portion acts as a trap to prevent liquid in the vessel from draining into the valve, except when the valve connects the vessel to the vacuum manifold. The trap also prevents cross-contamination between reaction vessels.

Vessel 12a, which is representative, has a base 52 which is designed for sealed, removable attachment to fitting 44, conventionally. A filter 54 located in the bottom portion of the vessel is effective to filter solid-phase particles used in biopolymer synthesis reactions described below. Typically, the particles are resin or glass beads having diameters between about 30 and 150 microns. The vessel capacity can be selected according to desired reaction volume, e.g., 10–50 ml. One exemplary vessel is a 18 ml glass tube having 20 micron pore-size polyethylene filter, and commercially available from Kontes (Vineland, N.J.). The reaction tubes may be formed with side wall bulges (not shown) in order to enhance turbulent mixing without bubble formation.

Valve 18a is mounted on platform 40 by an adapter 56 which engages a threaded opening 58 in the valve, as shown, and itself provides a threaded socket 60 in which manifold 34 (FIG. 1) is received. The manifold is a 5 to 1 connector which provides five tube channels, such as channel 59, in which the ends of the associated tubes, such as tube 30, are snugly received, when the manifold is tightened in the adapter. The tube channels are preferably arrayed at points equidistant from one another and from the center of the manifold. An exemplary adapter is a $\frac{1}{4}$" NPT female pipe adapter available from Cole-Parmer. The lower end of manifold is connected to the interior of the valve by a tube 62.

Valve 18a, which is representative, is a solenoid valve controllable by digital input signals between closed and open positions or conditions, indicated above. The valve in its closed position isolates the valve manifold from the gas and the vacuum manifolds, and in one and another open positions, communicates the valve manifold with either the vacuum manifold or the gas manifold. The valve receives fittings 64, 66 for tube connections to the vacuum and gas manifolds, respectively, as shown. Valves, such as valve 18a, the valve manifolds, such as manifold 34, and the tubes, such as tube 30 connected the valve manifold to the vessels, are also referred to herein valve means for communicating the vessels selectively with the vacuum and gas manifolds.

Figure 3A:
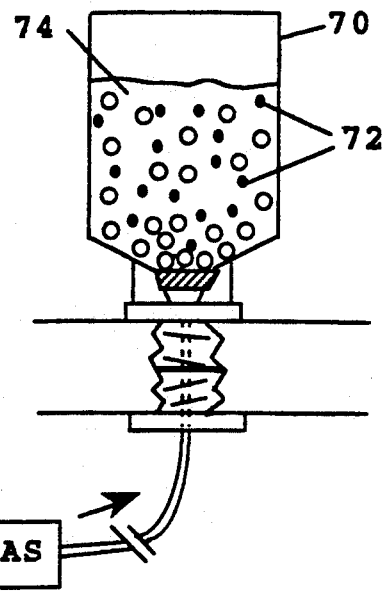
FIGS. 3A and 3B illustrate a reaction vessel in the FIG. 1 apparatus during a mixing step (3A), and a liquid-removal step (3B)
Figure 3B:
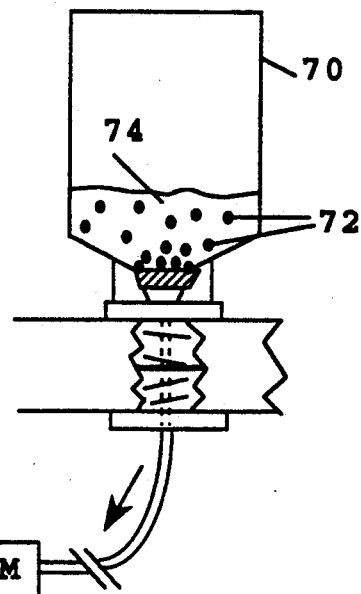

The operation of the apparatus is illustrated in FIGS. 3A and 3B. Initially, the control unit in the apparatus i set to act on a selected number of reaction vessels, over a selected number of reaction cycles, and at specified reaction times in each cycle. These settings determine which of the vessels will be placed in an active state for successive reaction mixing and liquid removing, the sequence of valve actuations, and the times between successive valve actuations. In a typical biopolymer synthesis operation, solid-phase particles derivatized with end-protected subunits are added to a selected group of reaction vessels. In the synthesis operation, a series of different reagent solutions, identified below, is added sequentially to each of the selected vessels, with each solution being mixed with solid-phase reaction particles in the vessels for a selected reaction period, then removed from the vessels by filtration, before addition of the next solution.

In the mixing step, illustrated in FIG. 3A for a representative reaction vessel 70, the selected vessels are communicated with the gas source, as described above. Gas influx through the vessel filters produces a controlled bubbling action which keeps solid-phase particles, such as indicated at 72, in an agitated, suspended state in a reagent solution 74, as shown. After a preset mixing period, the controlling valve(s) are switched to positions communicating the vessels with the vacuum source, causing the suspension liquid to be filtered from the vessel, as illustrated in FIG. 3B. After filtration, new reagent solution is added to the selected vessels, and the mixing and liquid-removal steps are repeated.

It is noted here that when the control valves are in a closed position, with liquid in the vessels, the upper trap portion of the tubes connecting the vessels to the valves prevent liquid from draining into the valves. It is also noted that the control unit operates to communicate only the particle-containing vessels with the gas and vacuum manifolds during operation.

Figure 4:
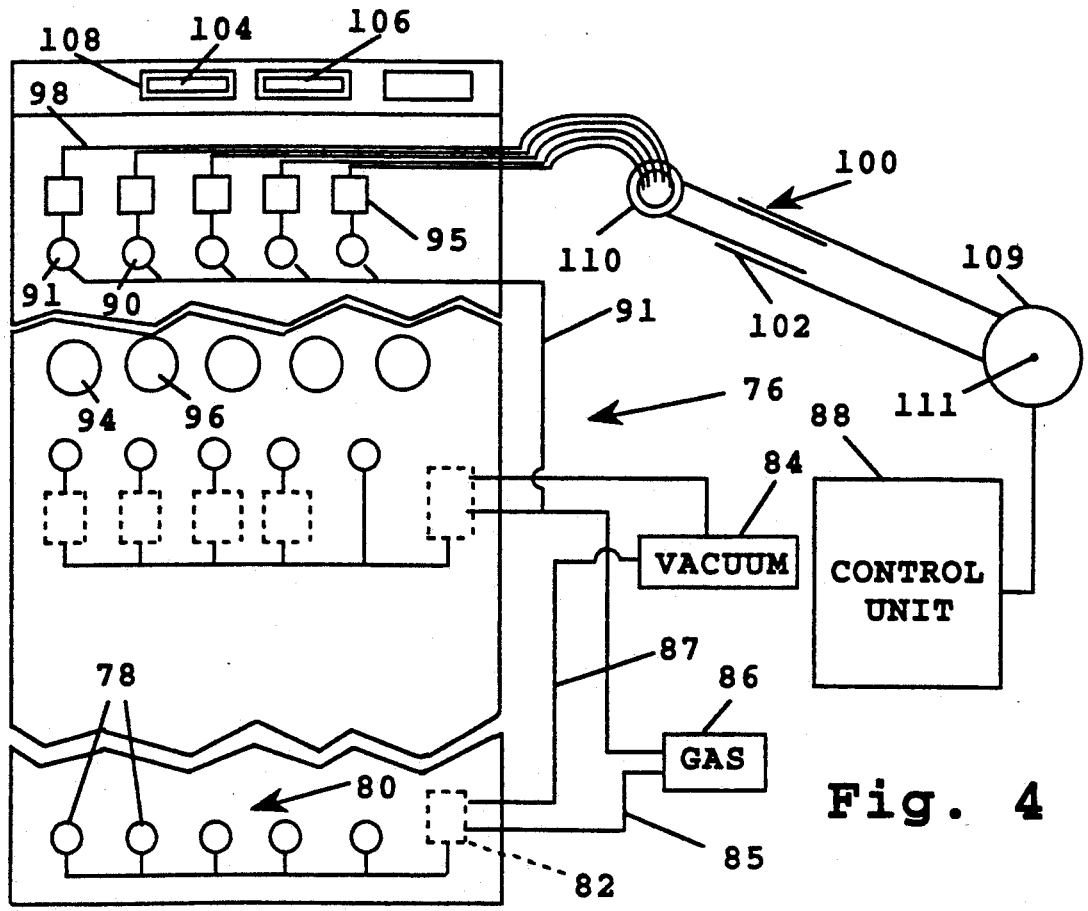
FIG. 4 is a diagrammatic plan view of a multi-vessel biopolymer synthesis apparatus constructed according to a another embodiment of the invention.

FIG. 4 is a schematic plan view of an apparatus 76 like the one just described, but provided with automated transfer means for adding reagent solutions successively to selected reaction vessels during a biopolymer synthesis reaction. The apparatus includes reaction vessels, such as vessels 78, which are configured in five-vessel sets, such as set 80, and controlled by valves, such as valve 82, as described above, for communication with vacuum and gas sources 84, 86, respectively, through gas and vacuum manifold, respectively. The valves are controlled by a microprocessor control unit 88, as described above.

The apparatus additionally includes a plurality of reagent vessels, such as vessels 90, 92, 94, and 96 for holding reagent solutions used in biopolymer synthesis. The reagent vessels are of two types: the first type, represented by vessels 90, 92, are designed for liquid dispensing, under pressure, by a solenoid valve, such as valve 95 associated with vessel 91. The vessels are pressurized by compressed gas from source 86, through a compressed line 91, as indicated. Valve 95, which is representative, is connected in-line to a dispenser tube 96 extending from vessel 91 to a delivery unit 110 to be described below. The tube may also include an in-line needle valve (not shown) for controlling rate of liquid flow through the tube. In a dispensing operation, the valve is opened for a timed interval, for dispensing a given volume of reagent solution from the vessel through the dispensing tube. The reagent vessels just described are used in dispensing various reagent solutions to the reaction vessels, in the operation of the apparatus described below.

The second type of reagent vessels, represented by vessels 94, 96, contain solutions of the selected sub-units used in biopolymer synthesis. For example, when the apparatus is used for polypeptide synthesis, these reaction vessels are used to hold the individual amino acids used for the synthesis. The subunit-solution reagent vessels are attached to the platform in the apparatus at fixed locations. When the apparatus is used for polynucleotide synthesis, the reaction vessels are used to hold individual activated nucleotide monomers, such as phosphoramidated nucleotides.

Also included in the apparatus is a robotic device 100 which is operable, under the control of unit 88, to transfer preselected volumes of solution from the solution vessels to a selected group of reaction vessels. The device has an extendable/retractable arm 102 which can carry one of a number of selected delivery units, such as units 104, 106 which are shown stored at pick-up station, such as station 108, on the platform, and unit 110 which is shown engaged at the end of arm 102. The unit 110 attached to arm 102 in FIG. 4 is a spigot unit which carries the ends of tubes, such as tube 98, from the reaction-solution vessels described above. One of the other units in the transfer device is a pipette unit which is designed for automated operation to (a) pick up a disposable pipette tip, (b) withdraw a selected volume of liquid from one vessel, (c) dispense the withdrawn liquid into another vessel, and (d) eject the pipette tip.

The robotic arm is mounted on a head 109 which is rotatable about an axis 111, and which is movable in a vertical direction along this axis for raising and lowering the arm. The distal end of the arm is designed for pick up and release of a selected delivery unit from station 108.

One preferred type of robotic device is a Zymate II Plus robot supplied commercially from Zymark Corp Hopkinton, Mass.). The delivery unit used in the apparatus is a Zymark "general purpose" hand which has two fingers which are capable of grabbing an appropriate spigot assembly and carrying it to reaction-vessel tubes, such as tube 98. Other units used in the apparatus are a Zymark 1-4 ml pipetting hand and a Zymark 0.2 to 1 ml pipetting hand. The robotic arm and associated delivery units are also referred to herein as a transfer device, or transfer means.

The control unit in the apparatus is a microprocessor which is programmed to actuate the control valves, and to direct the operation of the robotic arm according to user-specified settings. The design of the microprocessor program, and the requirements of the user interface, will be clear from the operation of the apparatus in biopolymer synthesis, as follows.

Figure 6:
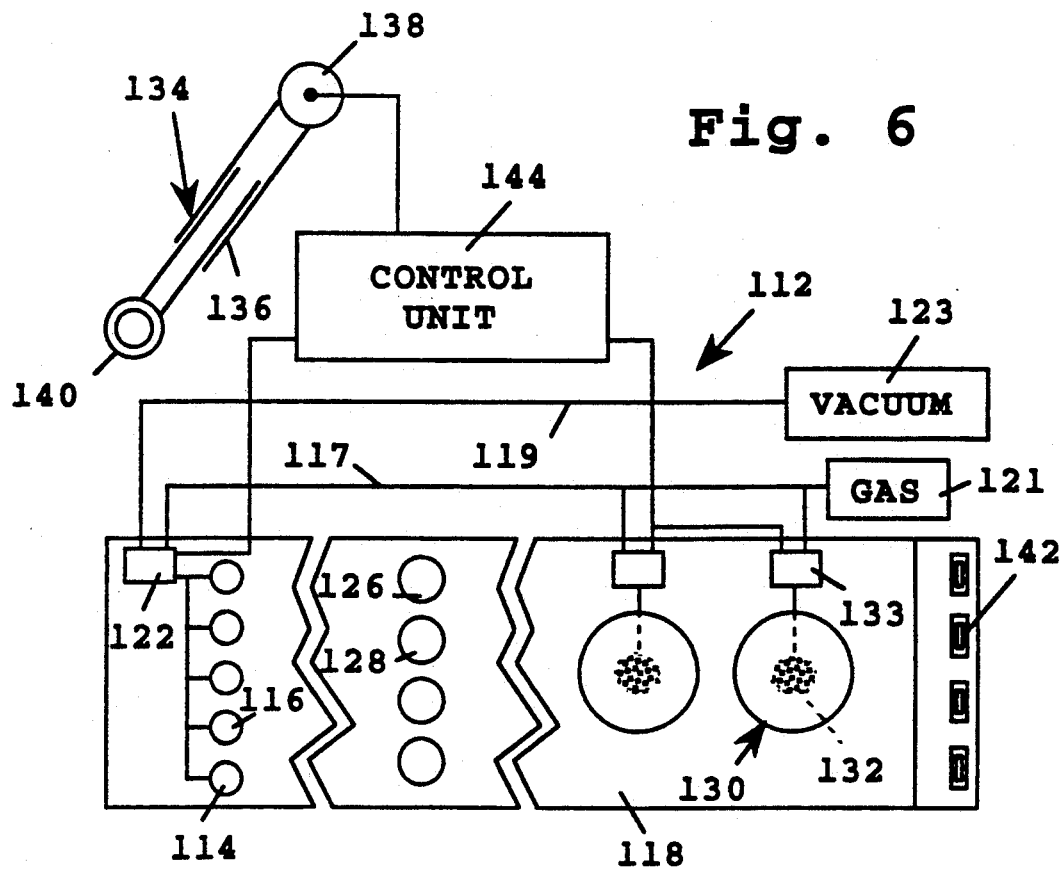
FIG. 6 is a diagrammatic view of a multi-vessel biopolymer synthesis apparatus constructed according to another embodiment of the apparatus of the invention.

The operation of the apparatus involves a predetermined sequence of solution cycles which together constitute a subunit-addition cycle, and a predetermined number of such subunit-addition cycles, each adding a new subunit to the growing particle-bound biopolymer in the reaction vessels. Initially, the user sets the control unit to specify the following subunit-cycle parameters: (a) the selected reaction vessels used in the operation, (b) the sequence of solution cycles (specified in terms of solution vessel positions), (c) the volumes of reagent solutions added to the reaction vessels in the subunit-addition, and (d) the mixing times at each cycle. The delivery subunit which is to be used in each solution cycle is dictated by the selected solution vessel. For example, the spigot unit in the embodiment described with respect to FIG. 6 is employed for all solution additions, except for the subunit and activating reagent solutions, which are added by a pipette unit. Also specified is the subunit sequence for each reaction vessel.

Figure 5:
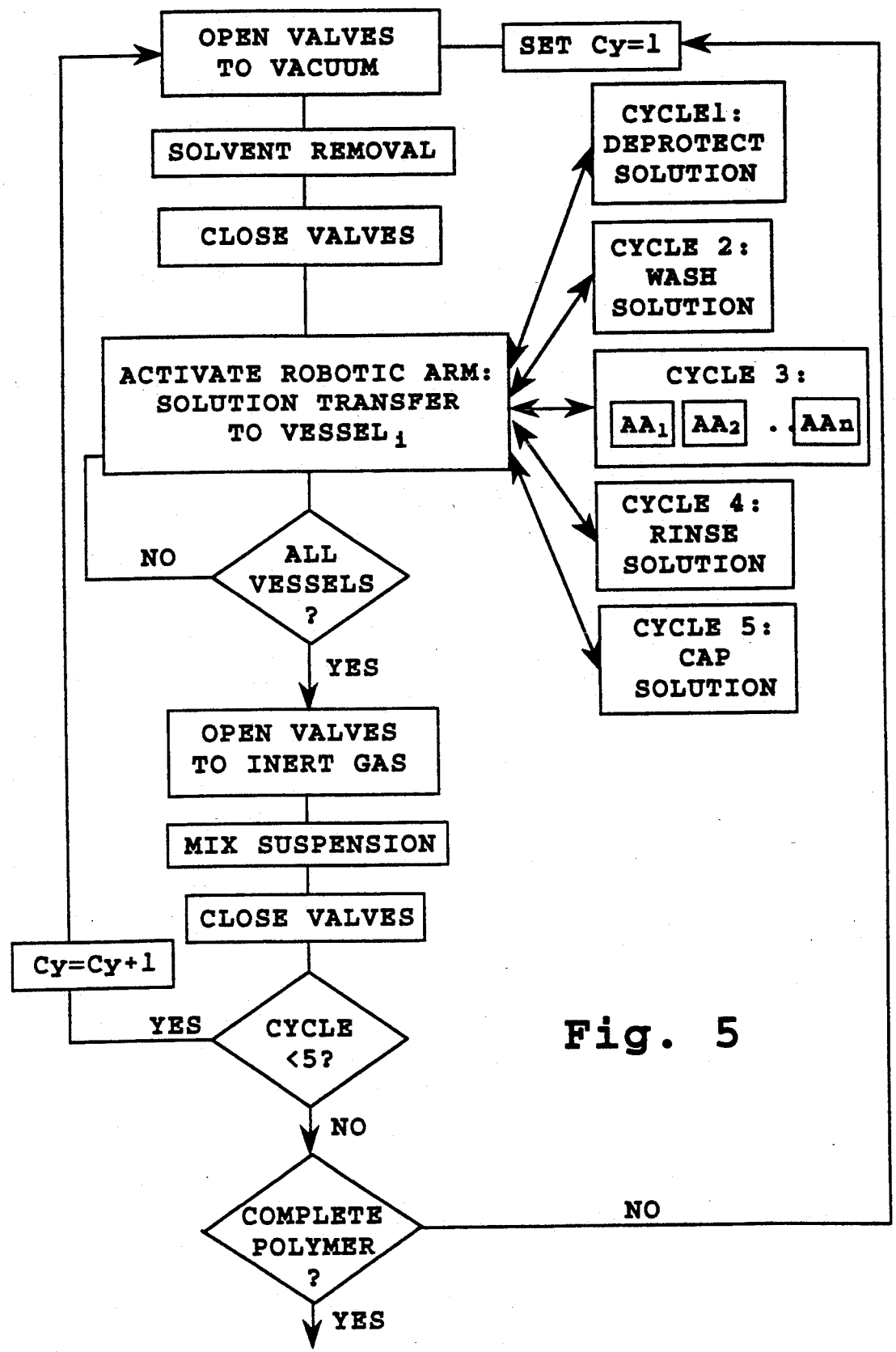
FIG. 5 is flow diagram of steps carried out by a control unit in the apparatus shown in FIG. 4, in a programmed operation for amino acid subunit addition.

FIG. 5 is a flow diagram of the steps in a complete subunit-addition cycle for use in amino acid subunit addition in polypeptide synthesis. In the first solution cycle (Cy=1), the control unit operates first to actuate valves for draining suspension fluid the designated vessels, by successive valve opening and closing. The robotic arm is now actuated to transfer deprotection solution, by successive arm movement to each of the designated reaction vessels, and dispenser actuation for solution delivery. After returning the arm to a parked position, the control unit operates to connect the reaction vessels with the gas source, for particle-suspension mixing as described above. The solution cycle terminates with closure of the valves. The operation now cycles through each successive reagent solution cycle, sequentially exposing the particles in the designated reaction vessels to a wash solution (cycle 2), a solution of a selected amino acid, plus a coupling reagent solution (cycle 3), a rinse solution (cycle 4), and a capping solution, to cap unreacted, deprotected subunits on the particle-bound subunits (cycle 5), as indicated.

After completion of one complete subunit addition cycle, the apparatus repeats the above steps, for addition of the next subunit Lo the particle-bound biopolymers. These subunit-addition cycles are repeated, adding a selected subunit to each polymer in a given reaction vessel, until biopolymer synthesis in each vessel is complete.

FIG. 6 is a schematic diagram of an apparatus 112 constructed according to another embodiment of the invention, for use in synthesis of biopolymers having mixed sequences, as described below in Section II. The apparatus includes plural reaction vessels, such as vessels 114, 116 mounted at fixed positions on a platform 118, and connected to gas and vacuum manifolds 117, 119, respectively, through valves, such as valve 122. The apparatus is designed for use with gas and vacuum sources 121, 123 by connection of the sources to manifolds 117, 119, respectively. The design and operation of the valved vessel configuration is similar to that described with respect to apparatus 10 above.

Also included in the apparatus are multiple reagent vessels, such as vessels 126, 128, for holding the different reagents needed in subunit addition synthesis. Selected reagent vessels are connected to solenoid-driven dispensers (not shown), as described with reference to FIG. 4, for dispensing measured liquid amounts to the reaction vessels. The apparatus further includes one or more mixing vessels, such as vessel 130, mounted at fixed positions on platform 118. Each vessel preferably has a volume capacity sufficient to hold the combined suspension contents of all of the reaction vessels.

Vessel 130, which is representative, has a bottom-portion frit or filter 132, through which compressed gas can be bubbled into the vessel for particle-suspension mixing in the vessel, and vacuum applied to the vessel, for removing liquid from the vessel. To this end, the vessel is connected to the gas and vacuum manifolds 117, 119, through a solenoid valve 133, as indicated.

Also included in the apparatus is a robotic transfer device 134, or means having an extendable arm 136 mounted on a swingable, vertically positionable base, as described above. The distal end of the transfer device is designed to operate with one of a variety of delivery units, such as unit 140 shown attached to the arm, and unit 142 stored on the platform. The transfer device, including the delivery units used for transferring liquid from the solution vessels to designated reaction vessels, are similar to device 100 described above.

The valves and robotic device in the apparatus are under the control of a microprocessor control unit 144. The software instructions used in unit, and the requirements of the user interface, are similar to those described with respect to apparatus 100, with the following added operations which will be described with reference to the flow diagram in FIG. 7.

Figure 7:
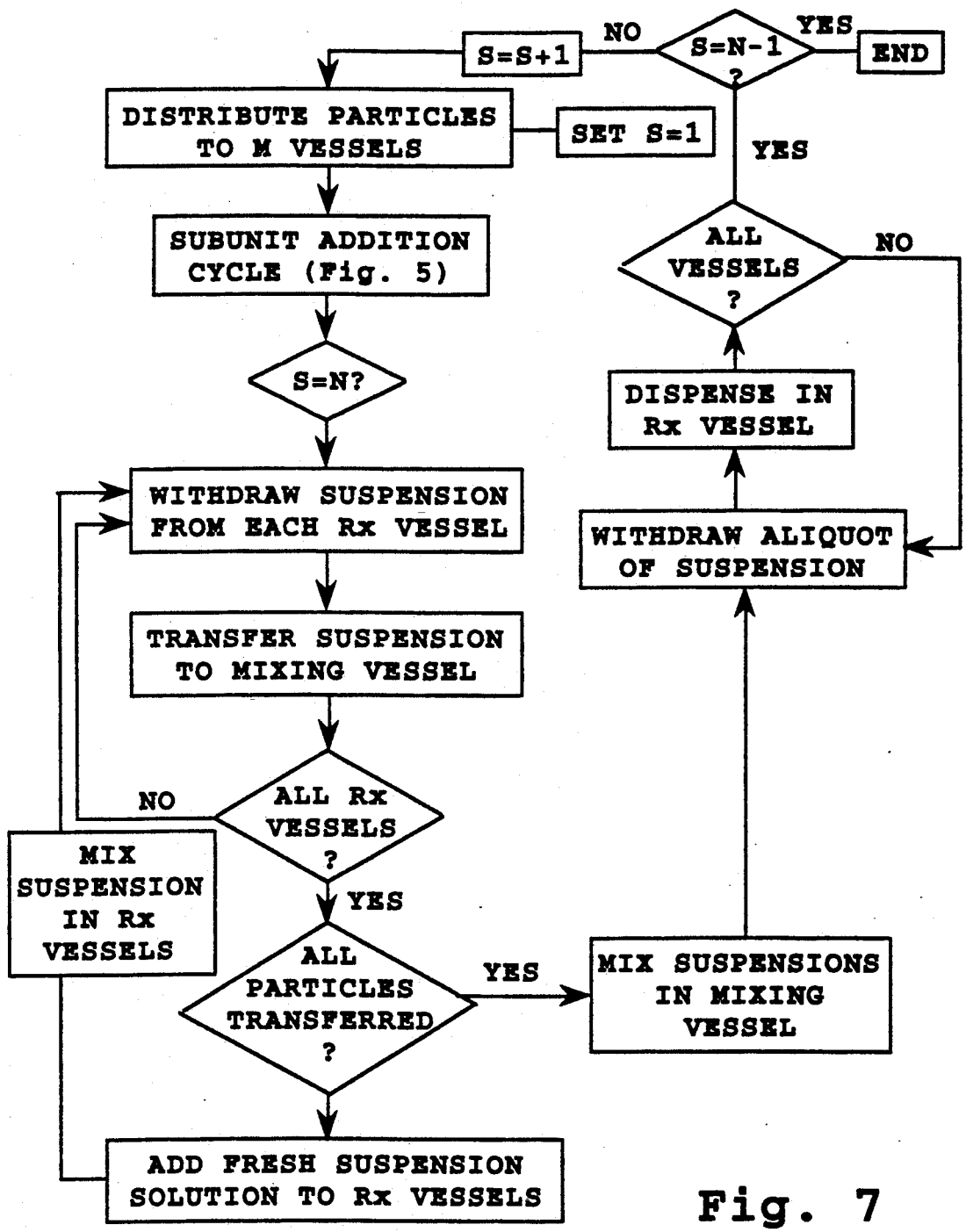
FIG. 7 is a flow diagram of steps carried out by a control unit in the apparatus of the invention, in a programmed operation for the synthesis of polypeptides having up to $M^N$ different sequences.

The FIG. 7 operation illustrates apparatus steps for automated synthesis of polypeptides having up to M different amino acids at each of R residues. That is, the final polypeptide mixture may include up to $M^R$ different-sequence polypeptides. Initially, particles with bound, N-protected amino acids are added to each of M reaction vessels. The particles added to each reaction vessel preferably contain an equimolar mixture of M different N-protected amino acids. The control unit is initialized as above, and additionally to set the desired particle-mixing cycles, as will be seen.

With the subunit-addition cycle set to 1, the control unit directs the sequence of valve, dispenser, and transfer-device operations in a subunit-addition cycle, i.e., a sequence of solution cycles, as described above with reference to FIG. 5. With each subunit addition cycle, an additional subunit is added to the end-terminal particle-bound subunits, typically one of M different amino acids in each reaction vessel.

At the end of the first subunit addition cycle, the control unit directs the robotic device in a series of operations which result in the transfer of the particle suspension in each reaction vessel to a mixing vessel. These operations direct the robotic device to (a) attach a pipette unit to the robotic arm; (b) pick up a fresh pipette tip, (c) move to a selected reaction vessel, (d) withdraw the particle suspension from that reaction vessel, (e) move to a mixing vessel, (f) dispense the withdrawn suspension into the mixing vessel, and (g) repeat steps (c)-(f) until all of the particle suspensions have been withdrawn. This is followed by addition of a given volume of fresh suspension liquid to each reaction vessel, with mixing to suspend residual particles in the vessel, followed by one or more additional suspension transfers from the reaction vessels to the mixing vessel, until essentially all of the resin particles have been transferred from the reaction vessels.

The control unit now actuates the mixing vessel valve to remove suspension fluid, directs the robotic arm to add fresh suspension solution to the mixing vessel, and actuates the mixing valve to produce mixing of the particles in the freshly added solution. The liquid level in the mixing vessel is brought to the exact necessary volume under the control of a liquid-level sensor (not shown) attached to the vessel.

At the end of this mixing step, the robotic device is directed in a series of operations which result in distribution of the mixing vessel contents back to the individual reaction vessels. Here the control unit directs the robotic device to (a) attach a pipette unit to the robotic arm; (b) pick up a fresh pipette tip, (c) move to the mixing vessel, (d) withdraw an aliquot of the particle suspension from the mixing vessel, (e) move to a selected reaction vessel, (f) dispense the withdrawn suspension into the reaction vessel, and (g) repeat steps (c)-(f) until the particle suspension in the mixing vessel has been distributed to each of the selected reaction vessels.

The apparatus has now returned to its original condition, with each reaction vessel containing a mixture of N-protected, particle-bound subunits. The entire cycle is repeated $R-1$ times until all R residues are added.

The maximum number of different-sequence peptides that can be formed in the apparatus will be limited by the number of resin particles which the apparatus can accommodate in both the mixing and reaction vessels. Typical polystyrene resin particles useful for polypeptide synthesis have a particle diameter of about 40 microns, and a 1 ml suspension can accommodate at most about $10^7$ such particles. Employing 50 ml of a particle suspension, about 900 mg of polypeptide can be synthesized.

From the foregoing, it will be appreciated how various objects and features of the apparatus invention are met. The multi-vessel apparatus described with respect to FIG. 1 allows for large-scale, simultaneous synthesis of up to 20 or more different biopolymers, with automatically timed mixing and solution removal after addition of each solvent. For example, employing 18 ml reaction vessels, it is possible to synthesize up to about 300 mg polypeptide per vessel in the apparatus.

The apparatus described with respect to FIG. 4 provides the same advantages, and additionally, a completely automated operation for biopolymer synthesis. According to one advantage of the apparatus, particle mixing during the subunit coupling step in the several reaction vessels can be timed so as to ensure substantially complete subunit addition in all of the vessels. Further, based on known coupling rates for each pair of amino acids, the control unit can operate to provide minimum coupling times needed at each reaction step to ensure complete subunit addition in each reaction vessel.

FIGS. 8A-8G are HPLC chromatograms of seven gramicidin S peptide analogs formed by the apparatus described in FIG. 4. Briefly, resin derivatized with arginine (R-Mts) was added to each of seven reaction vessels, and successive subunit additions were employed to add: valine at the first cycle; proline at the second cycle; d-phenylalanine or d-alanine at the third cycle; leucine or d-alanine at the fourth cycle; leucine or phenylalanine at the fifth cycle; valine at the sixth cycle; proline at the seventh cycle; d-phenylalanine, d-alanine, or serine at the eighth cycle; and leucine or alanine at the ninth cycle, as indicated in the figure. As seen from the figure, substantially pure polypeptide was formed in each reaction vessel. Amino acid analysis of the seven peptides confirmed the amino acid composition.

The apparatus described with respect to FIG. 6 provides, in addition to the features described above, operation for automated synthesis of equimolar amounts of mixed-sequence biopolymers having different sequences, in accordance with the biopolymer synthesis method disclosed in Section II below. As will be appreciated from Section II, the operation of the apparatus can be preset for synthesis of any combination of sequences having up $M^R$ different sequences, and in preselected molar ratios.

Although the operation of the apparatus has been illustrated with respect to polypeptide synthesis, it will be appreciated that the apparatus is intended for automated synthesis of other biopolymers, such as polynucleotides, which are constructed by subunit addition to end-protected subunits carried on a solid-phase particle. The use of the apparatus for automated mixed-sequence polynucleotides will be described in Section II below.

II. Automated Mixed-Particle Biopolymer Synthesis Method

The apparatus of the invention may be used for synthesizing different-sequence biopolymers, in accordance with another aspect of the invention. The mixed-resin synthesis method will be described with particular reference to apparatus 112 illustrated in FIG. 6, which has the following features required for the method:

(a) a mixing vessel, such as vessel 132, (b) multiple reaction vessels, such as vessels 116, (c) reagent vessels, such as vessels 126, 128, (d) transfer means for distributing a selected volume of particle suspension in the mixing vessel to each of the reaction vessels, for transferring a particle suspension from each reaction vessel to the mixing vessel, and for transferring selected reagent solutions from the reagent vessels to the reaction vessels, (e) means for coupling a selected free subunit to the terminal, particle bound subunits in each of the reaction vessels, and (e) control means for controlling the operation of the transfer means and coupling means.

The method employs solid-phase particles, such as polystyrene spheres, which are suitable for solid-phase biopolymer synthesis. In a typical method, batches of particles are derivatized with a selected end-protected biopolymer subunit, such as an N-protected amino acid, or a 5'—OH protected nucleotide, according to conventional derivatization methods. In the method illustrated in FIG. 9, five different batches of resin particles, indicated by solid squares, are derivatized with five different N-protected amino acids: glycine (G), lysine (K), glutamic acid (E), phenylalanine (F), and serine (S). The N-protected amino acids derivatized to the particles are also referred to herein as terminal, N-protected subunits.

The batches are combined in equimolar portions, i.e., in portions containing equimolar amounts of the terminal subunits derivatized on the particles. In the FIG. 9 example, this produces a mixture of particles having equimolar amounts of coupled G, K, E, F, and S N-protected subunits. The mixed particles are suspended in a suitable suspension liquid to form a particle-suspension mixture, indicated by "M" linked to a solid square in FIG. 9. Preferably the particles are suspended, as discussed above, by introducing an inert gas from the bottom of the vessel.

As indicated above, a preferred suspension liquid for polypeptide synthesis polystyrene particles is a 1:1 mixture of DMF and methylene chloride. This liquid, being substantially isopycnic with polystyrene spheres, forms a particle suspension which is stable against particle settling, i.e., the suspension has a stable, substantially uniform particle density.

The particle-suspension mixture is now distributed in preferably equal volume amounts to each of a selected number of reaction vessels in the apparatus. Because of the uniform particle density of the suspension, this results in substantially equimolar amounts particle-bound, terminal subunits being added to each vessel.

Typically, the particle mixture is distributed into a separate reaction vessel for each different subunit which is to be added at the next-in-sequence residue position. In the FIG. 9 example, it is desired to couple five different selected amino acids onto the terminal subunits of the mixed particles; thus the mixture is distributed equally into five different reaction vessels. The initial distribution of particle suspension may be by hand or by automated transfer from a mixing vessel, as described in Section I.

In the next step of the method, the apparatus is operated to couple a selected subunit to the terminal subunits on the mixed particles in each of the selected reaction vessels. For amino acid coupling, the apparatus operates, as described above, to successively react the particles with (a) a deprotection solution, (b) a wash solution, (c) a selected amino acid plus a coupling agent, and (d) a capping reagent.

These reagents are delivered successively to a each reaction vessel by the transfer means, followed by valve actuation to the reaction vessels for bubbling and liquid removal, as described above. Reagents suitable for polynucleotide coupling are given in Section III.

Figure 9:
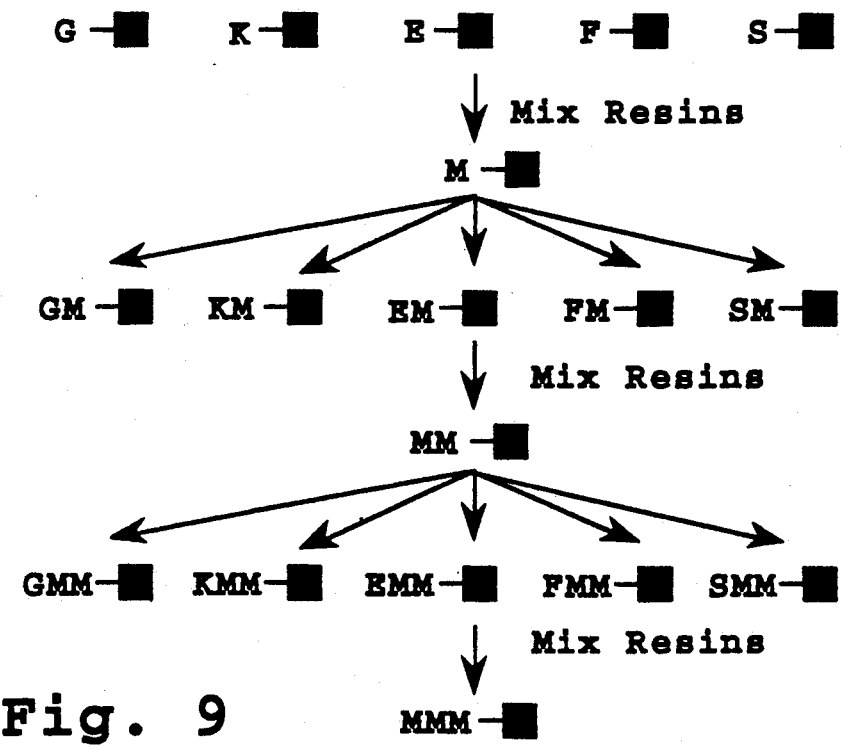
FIG. 9 illustrates the method of the invention for synthesis of different-sequence biopolymers, in accordance with the method of the invention.

In the FIG. 9 example, the mixed particles are reacted with one of the same five amino acids G, K, E, F, and S. Since each amino acid is coupled to each of five different terminal, particle-bound subunits, each reaction vessel now contains five different dipeptides.

As indicated above, the subunit coupling reaction is preferably carried out for a period sufficient to allow the slowest of the subunit addition reactions to run to completion. This ensures that all of the dimers formed by the reaction are represented in substantially equimolar amounts on the particles.

Following the completion of the first subunit-addition cycle, the particles in each reaction vessel are resuspended in a suitable suspension medium, and transferred by the transfer means to a common mixing vessel, for particle mixing. The mixture produced in the FIG. 9 example is indicated by "MM" linked to a solid square, and includes particles derivatized with one of $5^2$ dipeptides. The mixture is now redistributed by the transfer means into each of a selected number of reaction vessels, followed by coupling a new selected subunit onto the terminal particle-bound subunits, as above. In the FIG. 9 example, the same five amino acids are coupled to the particle-bound dipeptides, yielding 25 different-sequence tripeptides in each reaction vessel. The particles in each reaction vessel are again resuspended, transferred to a common mixing vessel, and mixed to form a particle mixture derivatized with $5^3$ different tripeptides, preferably in substantially equimolar amounts.

The distributing, coupling, and mixing steps are repeated until biopolymers of a desired number of subunits are formed on the particles. Thereafter, the particle-bound subunits may be deprotected or otherwise processed, and released from the particles according to conventional methods.

The method just described with reference to FIG. 9 illustrates the method of automated synthesis of up to $M^R$ different sequences, where up to M different residues are coupled to a mixed resin at each coupling cycle, and the coupling cycle is repeated R−1 times. It will be appreciated that the automated method can be varied, by suitable control unit instructions, to carry out synthesis with variations of the procedure. For example, in some coupling cycles, the same amino acid may be added to all reaction vessels, to produce invariant residue positions. Further, the number of reaction vessels employed may vary from cycle to cycle, where it is desired to achieve different degrees of variability at each residue position For example, at one cycle only five amino acid variations may be desired, and at another, all 20 variations.

III. Mixed-Particle Biopolymer Synthesis Method

This section describes more general aspects of the mixed-particle biopolymer synthesis method, and applications of the method to polypeptide and polynucleotide biosynthesis. The method includes the basic steps of: forming a particle-suspension mixture composed of a suspension of solid-phase particles derivatized with different terminal particle-bound biopolymer subunits; distributing the mixture into a plurality of separate reaction vessels; coupling a different selected subunit to the particle-bound terminal subunits in each reaction vessel; and mixing the suspensions from the plural reaction vessels to form a new particle suspension mixture. The distributing, coupling, and mixing steps are repeated at each biopolymer residue position where subunit variation is desired.

In one preferred embodiment, approximately equimolar amounts of the different-sequence biopolymers are generated, at each subunit addition step. This is accomplished by (a) adding approximately equimolar amounts of particle-bound biopolymer chain to each reaction vessel, and (b) carrying out the subunit addition reaction substantially to completion in each reaction vessel. As indicated above, the first of these conditions can be met by adding substantially equal volumes of a uniform particle density suspension to each reaction vessel.

The second condition is met by adding excess free subunits and employing reaction times (and temperatures) which lead to complete subunit addition of the slowest of the subunit addition reaction. Thus, for example, in synthesizing a polypeptide, where different amino acid subunits are added to each of several different reaction vessels, and where each of the 400 possible amino acid-to amino acid couplings is expected to have its own characteristic coupling rate, each vessel is allowed to react for a time sufficient to allow the slowest subunit-to-subunit combination in the reaction vessels to reach completion.

Also in a preferred embodiment, the amount of each different-sequence biopolymer which is synthesized is sufficient to allow each different-sequence biopolymer to be analyzed for a selected property. In the case of polypeptides, this activity is typically a binding affinity measured with respect to a selected receptor molecule or antibody. Other activities which can be selected include enzyme inhibition, enzymatic or cofactor activity, membrane binding or translocation, nucleic acid binding, and the like. Where the polypeptide analysis is conducted solution-phase biopolymers, after release from the solid-phase particles, the amount must further be sufficient for analysis and retrieval in non-particle form. Typically, the method is carried out under conditions which produce at least about 100 pmoles of each different-sequence polypeptide, as discussed below.

In the case of polynucleotides, the activity of interest may involve the use of the different-sequence polynucleotides as primers, for hybridization, or as coding sequences in a suitable expression system, as discussed below. In the latter application, it will be appreciated, the molar amount of each different sequence polynucleotide can be quite small, e.g., in the picomolar range. Other activities include, for example, ribozyme and ribozyme-like activity, protein-binding activity, and the like.

IIIA. Polypeptide Synthesis Methods

In one general application, the method is employed for generating different-sequence polypeptides which can be used for structure-function analysis of polypeptides (or proteins) with known amino acid sequences. The peptide of interest may be an antigenic peptide, a peptide hormone, or an antibiotic peptide, such as gramicidin or valinomycin. Typically, in structure-function studies, it is desired to determine the effect on activity of one of a variety of amino acid substitutions at one or more selected residue positions. Usually, the residue positions of interest are those which are semi-conserved or non-conserved in a family of analogous peptides.

By way of example, gramicidin S is an open-chain peptide having the primary structure:

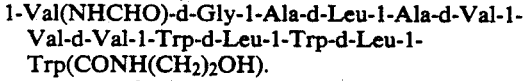

In structure-function studies, it may be of interest to determine the effect of all possible amino acid substitutions at the two d-Val positions. To produce the desired peptide analogs, particles are derivatized with the N-terminal pentapeptide 1-Val-d-Gly-1-Leu-d-Val-1-Ala, by conventional means. The particles are then distributed in equimolar amounts to each of 20 reaction vessels, and coupled separately to the 20 d-amino acids. After coupling, the particle suspensions are pooled and then reacted, either in separate reaction vessels or in a single vessel, with an 1-Val subunit, to produce a heptapeptide having 20 different amino acid combinations at the 6-residue position, and a Val at the 7-position residue.

The particles from above are mixed and redistributed to each of 20 different reaction vessels, where 20 different d-amino acids are coupled to the terminal subunits on the particles. The resulting octapeptides have 20 different amino acid combinations at the 6-residue position, a single Val at the 7-position residue, and 20 different amino acid combinations at the 8-position (N terminal) residue, and thus constitute a total of 400 different-sequence peptides. The peptides may be completed by conventional synthesis in which the final seven residues are coupled to the peptides batchwise.

After release of the peptides, and suitable N- or C-terminal modification, the peptides in each of the 20 reaction vessels are tested for antibiotic and/or ion transport activity, using standard assays. Each peptide tested has a common 8-position d-Val substitution and all 20 6-position d-Val substitutions. After systematically ranking the activities of the 20 groups, a new group of peptides which differ only at the 6-position, and have a selected 8-position substitution) can be synthesized, as above, for further structure-function studies.

It will be appreciated that the method provides a rapid and systematic method for generating large numbers of peptide analogs containing desired substitutions at selected residue positions.

In another general application, the synthesis method is used to generate random-sequence polypeptides for selecting peptides with desired activity, typically binding activity to a known receptor, such as an antibody. The method may be used to generate every possible combination of 20 different acids (which may be L-amino acids, D-amino acids or D- or L-amino acid analogs) at each R residue position. The solid-phase particles in this method are preferably formed from a mixture of particles, each containing one of the 20 possible L-amino acids, in equimolar amounts. This mixture is distributed to each of 20 reaction vessels, for addition of one of the 20 L-amino acid subunits to each particle mixture. After subunit addition, the particles are combined and redistributed to 20 reaction vessels, for addition of the third amino acid. The procedure is repeated $R-1$ times for synthesis of the desired R-residue polypeptides.

The peptides will contain 400 members if the peptide is a dipeptide; 8,000 members, if a tetrapeptide; 160,000 members, if a tripeptide, and so forth. The mixtures, in order to be subjected to procedures for selection and analysis, must provide enough of each member to meet the requirements for selection and analysis. Typically, about 100 picomoles of a peptide are needed in order to select the peptide and to analyze its primary structure. The total amount of protein mixture required to produce 100 picomoles of each peptide can be readily calculated, and corresponds approximately to 2.2 $\mu$g for 400 dimers, 0.44 mg for 8,000 trimers, 8.8. mg for 160K tetramers, 176 mg for 3.2 million pentamers, and 3.5 g for 64 million hexamers. Thus, even for a peptide of 6 amino acids, only about 3.5 g of total mixture is required. Since many immunoreactive peptide species are 5-6 amino acids in length, it can be appreciated that the method is suitable for generating "mimetopes" which are immunoreactive with selected receptors, such as antibodies. This method is feasible even for larger peptides, when conserved regions, i.e., positions with fixed amino acids, are present.

By way of example, the synthesis of the following peptide mixture is described: Fifty nmoles of each of the 5 amino acid resins, Asp, His, Gln, Phe, and Leu were weighed out based on their substitution, mixed as a thin slurry in DMF (approximately 1 g/40 ml) and shaken by vortexing for 1 hr, followed by washing with methylene chloride (approx. 100 ml) and drying under vacuum. The resin mix was then distributed equally into 5 reaction vessels.

The Fmoc-N-protected amino acids attached to the particles were deprotected by incubation with 20% piperidine in DMF (2×3 ml, for 10 min each), followed by extensive washing (3×3 ml of DMF, followed by 3×3 ml of methanol, and 3×3 ml DMF). To each reaction vessel was added 0.25 mmoles of activated amino acid. For ease of synthesis, the activated amino acids were added as preformed pentafluorophenyl esters (OPfp esters), except for serine and threonine, which were added as the preformed 3-hydroxy-4-oxo-3,4-dihydrobenzotriazine esters (ODHBt esters). 0.2 ml of 0.5M HOBt in DMF was added to each coupling reaction. The reactions were allowed to proceed for 2 hrs. Excess amino acid was aspirated away, and the resin washed with DMF (3×3 ml) followed by methanol 3×3 ml). The completeness of each of the coupling reactions was verified by qualitative ninhydrin (triketohydrine hydrate) which, if negative, indicates greater than 99% coupling (Kaiser).

Figure 10:
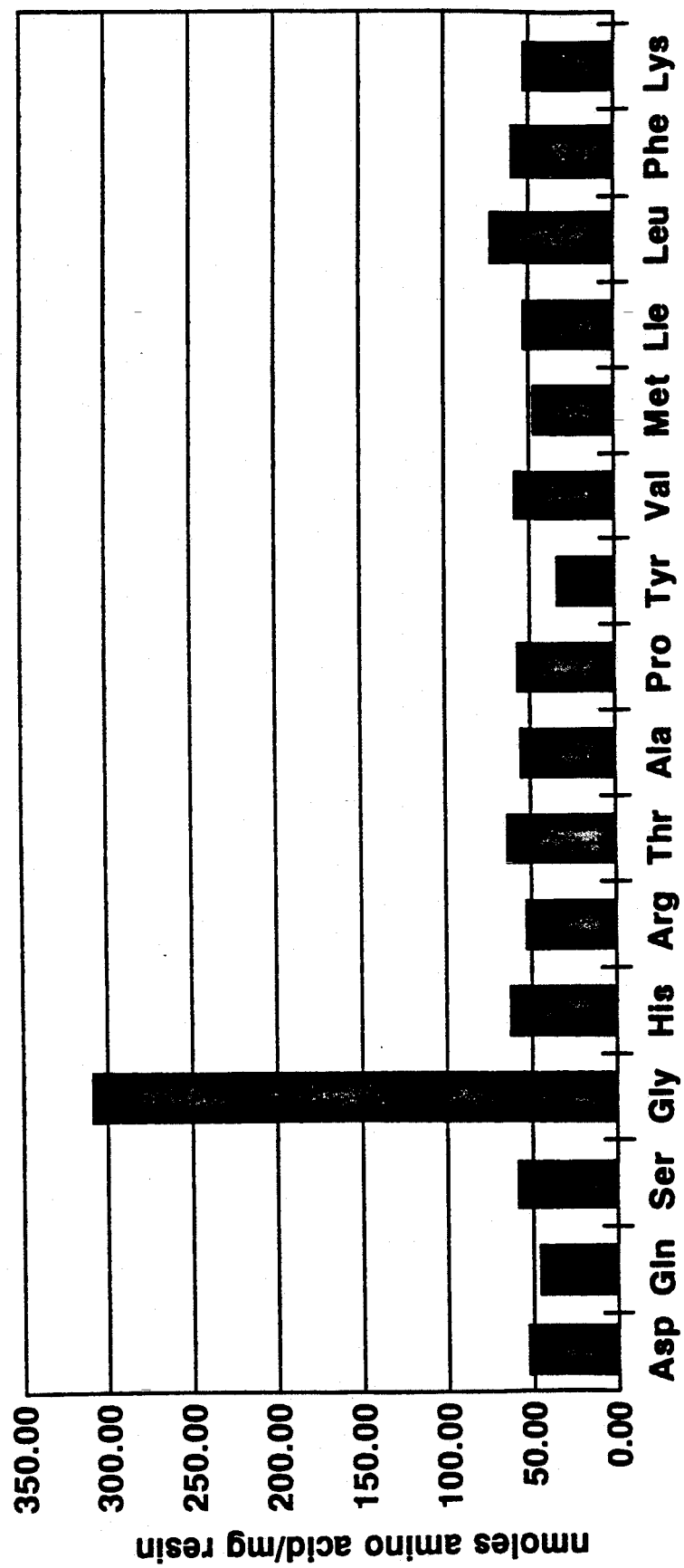
FIG. 10 is a graph showing the amino acid composition of a peptide mixture prepared in accordance with the method of the invention.

The particles were then recombined, swollen in DMF and mixed as described above. In cycles 2 and 4, which required mixtures, the resins were again split and treated as described above, with the appropriate amino acids coupled. At position 3, a single amino acid, glycine, was desired. The particles were combined and glycine was coupled to the entire particle mixture in a single reaction. Characterization by amino acid analysis (Bidling-meyer) of the final peptide product or the peptide mixture described above shows the peptide to have the amino acid composition shown in FIG. 10. It can be seen that all of the amino acids, with the exception of glycine, are present in substantially equimolar amounts, indicating synthesis of a substantially equimolar mixture of polypeptides. Glycine, as predicted, is present in a 5 fold greater amount than the other amino acids. Tyrosine appears somewhat low, possibly due to tyrosine oxidation during hydrolysis.

Figure 11A:
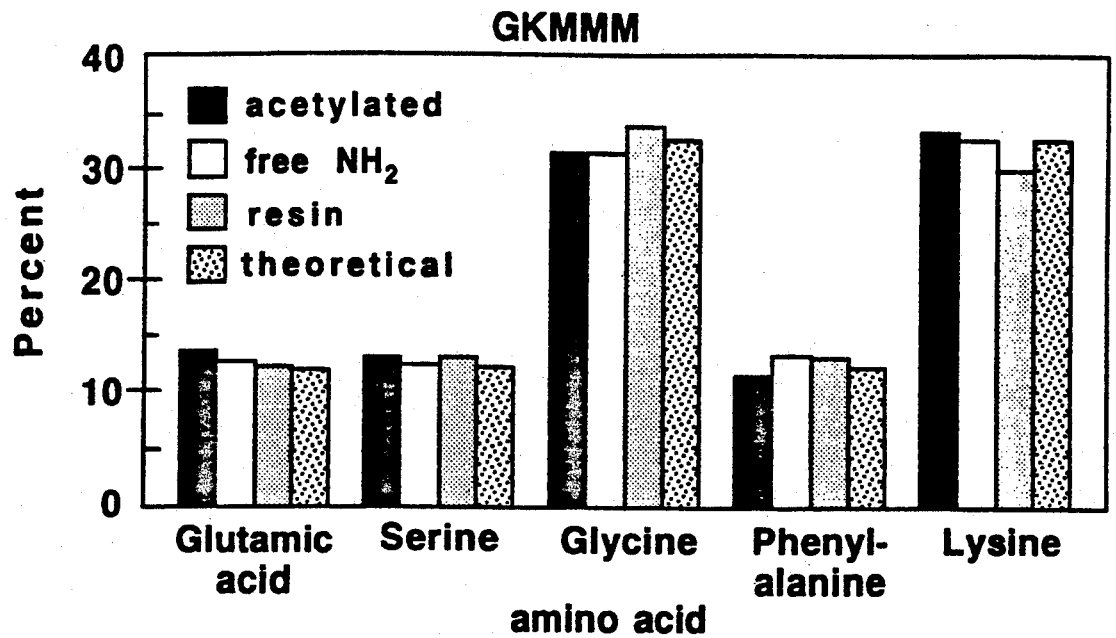
FIGS. 11A and 11B are graphs showing the percent amount of certain amino acids in pools.
Figure 11B:
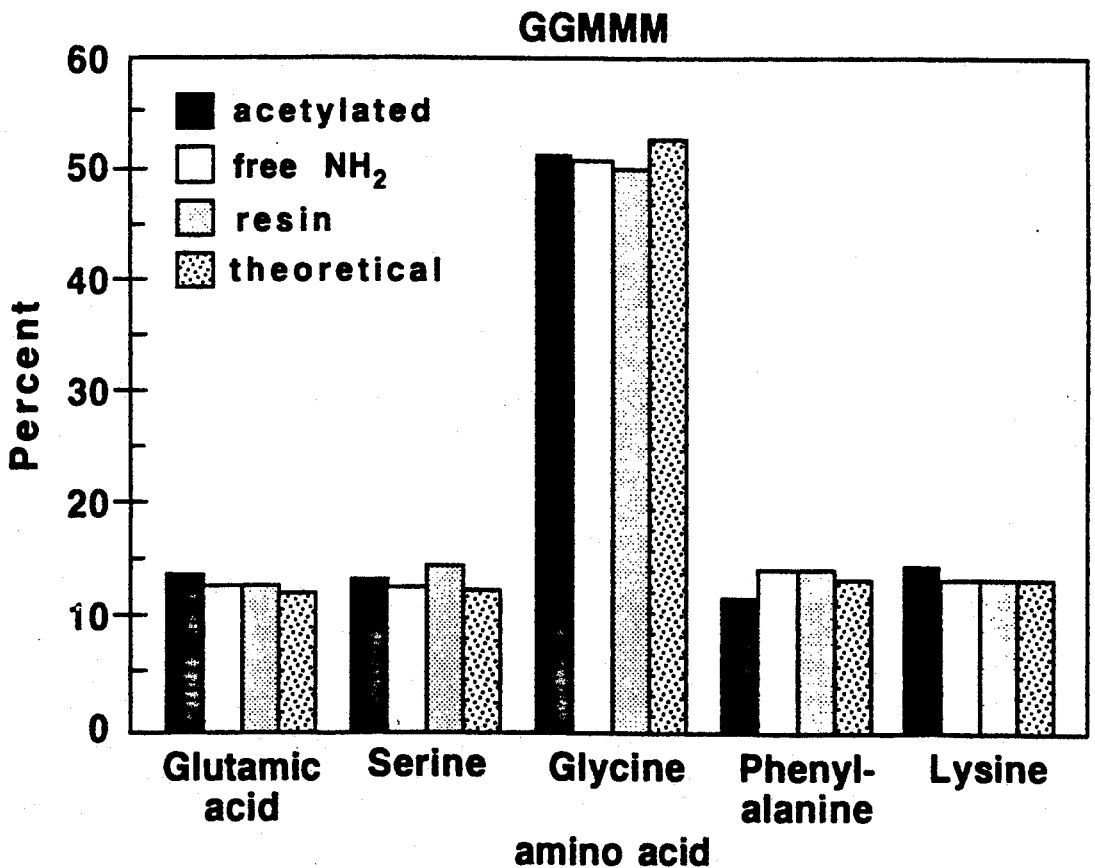

A second set of peptide mixtures was similarly synthesized. In this case, all possible combinations of pentamers using the amino acid basis set of Gly, Lys, Glu, Phe, and Ser were synthesized. These were synthesized in 25 pools, each containing 125 different peptides. The synthesis was designed so that each pool contained the same amino terminal amino acids and equimolar mixes of all 5 amino acids at the other 3 residues (e.g., GG-mix-mix-mix, GK-mix-mix-mix, SF-mix-mix-mix, etc. ). The synthesis was carried out using the methodology illustrated above. FIGS. 11A and 11B show the amino acid analysis results for 2 of the 25 pools. The theoretical values for each amino acid based on the expected composition of the pool are shown next to the values obtained. It can be seen that the actual amino acid composition of the pools agrees closely with the theoretical, further demonstrating the usefulness of this method for synthesis of equimolar polypeptide mixtures.

It will be appreciated that the method is also applicable to other amino acid residues, or suitable subunits, such as hydroxyproline, n-aminoisobutyric acid, sarcosine, citrulline, cysteic acid, t-butylglycine, t-butylalanine, phenylglycine, cyclohexylalanine, 8-alanine, 4-aminobutyric acid, and the like, as well as D forms of amino acids. It will also be appreciated that the number of pools created at subunit addition cycle can be varied. Thus, although 20 pools might be created for the first step reaction, the particle mixture amy be divided into only 5 fractions for the second subunit addition, given 20 different amino acid variations at position 2 and 5 at position 3It will be understood that the apparatus may be provided with more than 20 reaction vessels, if needed to accommodate more than 20 different monomers, e.g., all L- and D-amino acids.

Isolation of full-length peptides can be further aided by utilizing a final amino acyl residue which is blocked with a selected group such as tBoc-biotin, which allows polypeptide isolation by affinity chromatography on an avidin or streptavidin solid support. The use of such an affinity group in the final position ensures isolation of full-sequence peptides.

The method of the invention results in a complex mixture of different-sequence peptides. From this mixture, one or more peptides having a desired activity are selected. Typically, the desired activity is a given binding affinity for a receptor, such as an immunoglobulin, glycolipid, receptor protein, or enzyme. The peptides can be screened for the desired binding activity conventionally, e.g., by affinity chromatography in which the receptor is coupled to a solid support. Here the peptide mixture is contacted with the affinity support, and non-bound peptides removed by washing. The bound peptides are then released from the support by washing with high salt or other denaturants effective to disrupt the peptide-receptor binding.

Alternatively, peptides which are substrates for enzymes such as protease, can be separated from non-substrate peptides in the mixture on the basis of the size of cleavage products, or release of affinity labels from the peptides, or the like.

After isolation of peptides with desired binding activity, it may be further desirable to purify selected peptides, e.g., by HPLC. If large subpopulations are obtained by the screening, further screening at higher stringency may be useful. Thus, for example, if a mixture of peptides binding to a given antibody or receptor contains fifty or so members, salt concentration or pH can be adjusted to dissociate all but the most tightly bound members, or the natural substrate can be used to provide competition binding.

Standard methods of analysis can be used to obtain the information needed to identify the particular peptide(s) recovered, including molecular weight, amino acid composition, and amino acid sequence.

The method can be used for the synthesis and selection of antigenic polypeptides useful as diagnostic reagents or vaccines. In addition the peptides may be selected on the basis of their activity as peptide hormones, peptide antibiotics, or peptides with other therapeutic indications, according to their ability to bind to selected receptors, or to produce other selectable physiological effects which can be observed in a screening procedure.

IIIC. Polynucleotide Synthesis Methods

The method of the invention is also useful for synthesizing different-sequence polynucleotides, typically single-stranded DNA. General solid-phase reagents, protecting and deprotecting strategies, and coupling reaction reagents may be conventional. Typically, for example, controlled pore glass particles will be derivatized with a single 5'-OH protected single polynucleotide or trinucleotide. At each subunit addition cycle, the particles will first be reacted with dichloracetic acid, to deprotect the terminal nucleotide subunit, then washed to remove deprotection reagent, and reacted with a free phosphoramidite-activated 5'-OH protected nucleotide subunit, under conditions which favor substantially complete coupling of the subunits of the particle-bound, deprotected terminal subunit.

The subunits used in each coupling may be single nucleotides, or subunits formed of two or more defined-sequence oligonucleotides. In one preferred embodiment described below, the subunits are trinucleotides corresponding to selected codons, such as codons for each of 20 natural L-amino acids. In this embodiment, each subunit addition cycle is effective to add a three-nucleotide codon to the polymer. Thus, for example, to prepare a mixture of polynucleotides coding for a random sequence of R-residue peptides, the synthesis method would require $R-1$ subunit additions, with each of 20 different trinucleotide codon subunits being added to a particle mixture at each cycle.

In one general application, different-sequence oligonucleotides are prepared for use as degenerate primers for polymerase chain reaction (PCR) amplification of DNA. In a typical application, a protein having regions of known amino acid sequences is available, and it is desired to isolate and clone a genomic or cDNA fragment corresponding to (encoding) the protein.

The PCR method requires two sets of degenerate primers corresponding to spaced known-sequence regions of the protein. Each set is generated, in accordance with the invention, by preparing a resin particles derivatized with each of the 1-6 codons for the N-terminal amino acid in the selected known-sequence region. The particles are mixed, then distributed into 1-6 separate reaction vessels, depending on the number of degenerate codons of the next-in amino acid, and each mixture is then reacted with the 1-6 codons of this next-in codon, under conditions in which each codon subunit addition is substantially complete. The particles from these vessels, when combined contain all of the 1-16 possible codon sequence for the first two N-terminal amino acids in the selected known-sequence region of the protein.

The procedure is repeated, with mixing and redistributing the particle mixture into 1-6 reaction vessels with each subunit (codon) addition cycle, until the desired-length primer set is produced. Typically, at least about 12-21 nucleotides (3-6 cycles) are required for an effective PCR primer set.

Figure 12:
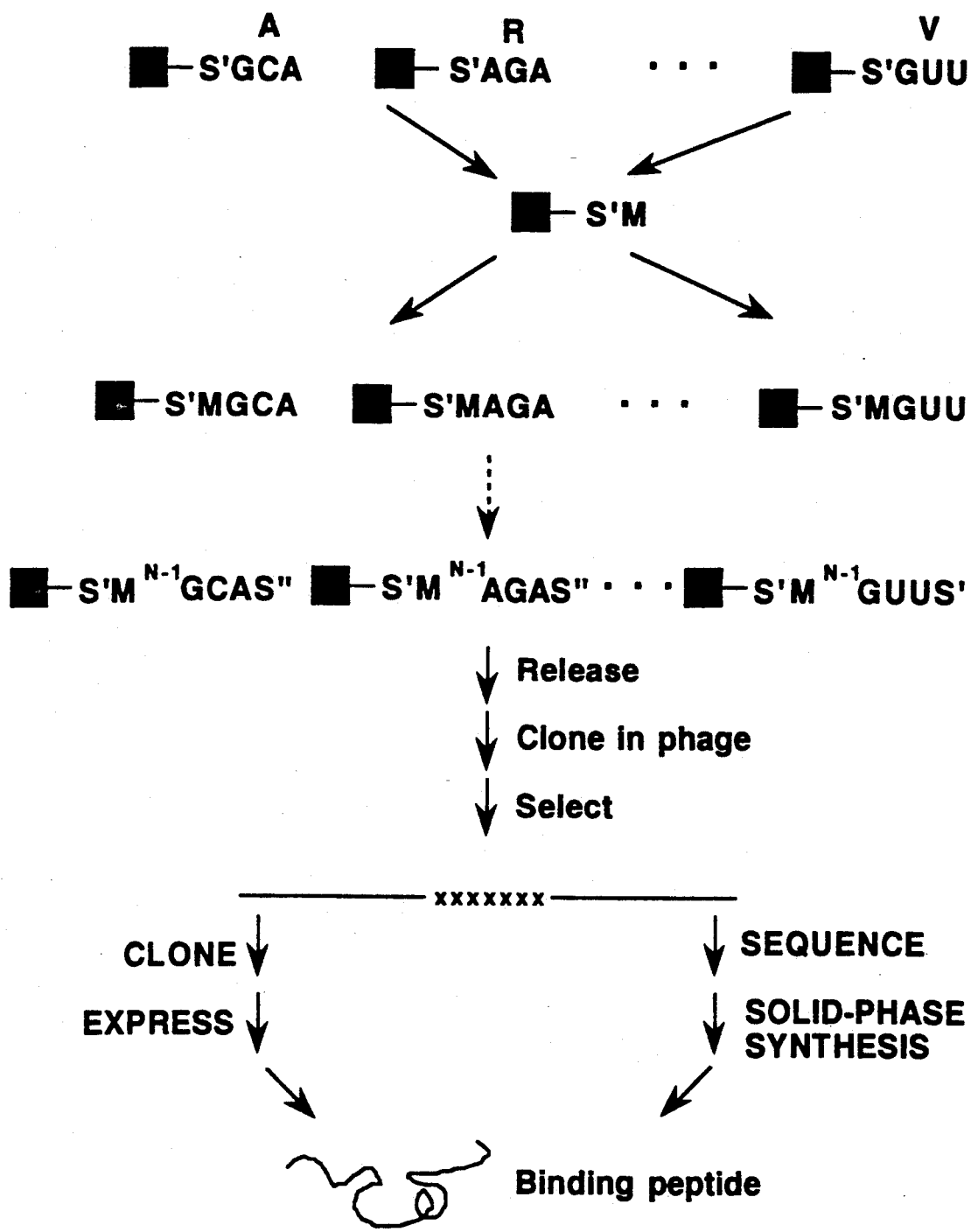
FIG. 12 illustrates steps in the synthesis and selection of a polynucleotide which encodes a polypeptide with selected binding activity.

A second general application of the method for synthesizing different-sequence polynucleotides is illustrated in FIG. 12. The aim of this method is to produce, isolate and clone a polynucleotide sequence which encodes a peptide having a desired activity, such as a selected binding activity. As a first step, the method of the invention is used to generate a mixture of polynucleotides encoding all (or at least a large number of) possible coding sequences of a peptide having a given size, e.g., 5-10 amino acid the residue polynucleotide synthesis follows the general approach outlined at the top of FIG. 12. Resin particles, indicated by solid squares, are prepared conventionally with the 5' sequence C TCT CAC TCC ($S_5$,). The resin is distributed to each of 20 reaction vessels where coupling to each of the 20 possible L-amino acids codons, such as trinucleotide GCA codon for alanine, AGA trinucleotide codon for arginine, and so on, is carried out. The particles from the 20 vessels are mixed and redistributed to 20 vessels, and the codon addition cycle is repeated. The mix and redistribute cycle is repeated a total of N times, producing a total of $20^N$ different sequences, as indicated.

After the Nth mixed-codon cycle, the resin is combined and further treated to place the sequence GGC GGC ACT, GTT, GAA, AGT, TGT-3' (indicated by 5") on each of the different-sequence polymers.

The polymers are released from the particles, annealed with suitable 3'-end and 5'-end oligonucleotides, and introduced into the StiI site of vector fUSE5 replicative form phage, as has been described (Cwirla). This construction places the random-sequence polynucleotides in the region coding for the N terminus of the pIII adsorption protein of fd phage. The phage are grown in a bacterial host, isolated, and then screened for binding activity to a selected receptor by an affinity technique known as panning (Parmley, Scott). The phage selected by this method thus have a coding sequence which encodes a peptide having binding affinity for the screening receptor. These phage may be further rescreened and purified, to obtain the desired coding sequence (indicated by xxxxx in FIG. 12). This coding sequence can be sequenced to determine the desired coding sequence.

Once the coding sequence is known, the corresponding-sequence polypeptide can be produced by conventional solid-phase methods, or the sequence can be employed in a conventional expression system for recombinant production of the protein.

From the foregoing, it will be appreciated how the objects and features of the invention are met. The mixed-particle method for biopolymer allows for synthesis of very large numbers of biopolymers, in substantially equimolar amounts, with relatively few subunit addition steps. Further, subunit variation may be generated selectively at different polymer positions, with some positions containing a single subunit, and other positions containing 2 to 20 or more different subunits.

The method is readily adapted to automated synthesis, employing the apparatus of the invention. In particular, once biopolymer sequence variation is specified initially to a control unit, the apparatus can function in a completely automated fashion to produce the desired biopolymer mixture.

Although the invention has been described with respect to particular polypeptide and polynucleotide methods and applications, it will be appreciated that various modifications of the methods and additional applications are possible without departing from the invention.

It is claimed:

1. Apparatus for use in synthesizing different-sequence biopolymers by sequential addition of biopolymer subunits to immobilized subunits carried on solid phase particles in a particle suspension, said apparatus comprising, in operative condition,
   (a) a mixing vessel,
   (b) multiple reaction vessels,
   (c) reagent vessels,
   (d) transfer means for distributing a selected volume of particle suspension in the mixing vessel to each of the reaction vessels, for transferring a particle suspension from each reaction vessel to the mixing vessel, and for transferring selected reagents from the reagent vessels to the reaction vessels,
   (e) means for coupling a selected free subunit to the terminal, particle bound subunits in each of the reaction vessels, and
   (f) control means for controlling the transfer means and coupling means for (1) distributing a mixed particle suspension in the mixing vessel to selected reaction vessels, (2) coupling a selected subunit to terminal particle-bound subunits in each reaction vessels, and (3) transferring the particle suspensions in the reaction vessels to the mixing vessel.

2. The apparatus of claim 1, for use in combination with a vacuum source, wherein each of said reaction vessels has a filter which defines a lower vessel surface which is adapted to retain the solid phase of such particle suspension when a vacuum is applied to the filter, and said coupling means includes valve means connecting the filter in each of said vessels to such vacuum source, positionable between a closed position, in which the vessels are isolated from the vacuum source, and an open position in which the valve means communicates the vessels in the set with the vacuum source, and said control means is operable to activate the valve means from its closed to its open positions.

3. The apparatus of claim 2, for use in combination with a source of compressed gas, wherein said valve means also connects each reaction vessel filter with such compressed-gas source, and is positionable to a second open position at which the valve means communicates each reaction vessel with the compressed-gas source, to produce mixing by bubbling within the vessels, and said control means is operable to activate the valve means to its second open position.

4. The apparatus of claim 3, wherein said reaction vessels include multiple sets of vessels, and said valve means includes, for each such set, a solenoid valve connecting the vessels in each set to such vacuum and gas sources.

5. The apparatus of claim 4, which further includes a set of vessels which are each connected to the vacuum and gas sources by individual solenoid valves, such that any selected number of vessels in the apparatus can be operated in a mode in which they are connected to valves which can be operated in such open positions, and the remaining vessels in the apparatus are connected to valves which can be operated exclusively in closed positions.

6. The apparatus of claim 4, wherein the valve means additionally includes, for each set of vessels, a manifold connected to said valve and a plurality of tubes connecting the manifold to each vessel in the set, where the tubes extend above a maximum level in the vessels which is reached when liquid is added to the vessels during operation of the apparatus in polymer preparation.

* * * * *